(12) United States Patent
Old et al.

(10) Patent No.: US 7,960,379 B2
(45) Date of Patent: Jun. 14, 2011

(54) THERAPEUTIC COMPOUNDS

(75) Inventors: David W. Old, Irvine, CA (US); Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 272 days.

(21) Appl. No.: 12/402,877

(22) Filed: Mar. 12, 2009

(65) Prior Publication Data

US 2009/0233931 A1 Sep. 17, 2009

Related U.S. Application Data

(60) Provisional application No. 61/036,511, filed on Mar. 14, 2008.

(51) Int. Cl.
*A61K 31/535* (2006.01)
*A61K 31/425* (2006.01)
*C07D 413/14* (2006.01)
*C07D 275/02* (2006.01)

(52) U.S. Cl. .............. 514/236.8; 514/372; 548/206; 544/133

(58) Field of Classification Search ............ 548/206; 514/236.8, 372; 544/133
See application file for complete search history.

(56) References Cited

U.S. PATENT DOCUMENTS

| | | | |
|---|---|---|---|
| 4,087,435 | A | 5/1978 | Cragoe |
| 4,166,452 | A | 9/1979 | Generales |
| 4,256,108 | A | 3/1981 | Theeuwes |
| 4,265,874 | A | 5/1981 | Donsen |
| 5,462,968 | A | 10/1995 | Woodward |
| 5,698,598 | A | 12/1997 | Woodward |
| 6,090,847 | A | 7/2000 | Woodward |
| 6,437,146 | B1 | 8/2002 | Hattori |
| 6,710,072 | B2 | 3/2004 | Burk |
| 7,091,231 | B2 | 8/2006 | Donde |
| 2007/0265321 | A1 | 11/2007 | Burk |

FOREIGN PATENT DOCUMENTS

| | | |
|---|---|---|
| WO | WO 93/14743 | 8/1993 |
| WO | WO 03/103604 | 12/2003 |
| WO | WO 2007/000641 | 1/2007 |
| WO | WO 2007/134085 | 11/2007 |
| WO | WO 2008/064039 | 5/2008 |

OTHER PUBLICATIONS

Carey, Francis A.: Organic Chemistry, New York: McGraw-Hill Book Company 1987, p. 63.
Remington's Pharmaceutical Sciences, Mack Publishing Company, Easton, pa., 16th Edition, 1980.
Resul, Bahram; et al.: Structure-Activity Relationships of Prostaglandin Analogues as Ocular Hypotensive Agents, Current Opinion in Therapeutic Patents, vol. 3, No. 6, Jan. 1, 1993, pp. 781-795.
Steinhuebel, Dietrich; et al.: Synthesis of N-arylated Sultams: Palladium- and Copper-Catalyzed Cross Coupling of Aryl Halides With 1,4-Butane and 1,3-Propanesultams, Tet. Lett. 2004, 3305-3307.
U.S. Appl. No. 60/660,748, filed Mar. 10, 2005, Old.

*Primary Examiner* — Rebecca L Anderson
(74) *Attorney, Agent, or Firm* — Kevin J. Forrestal; John E. Wurst; Doina G. Ene

(57) ABSTRACT

Compounds comprising

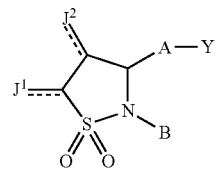

or a pharmaceutically acceptable salt or a prodrug thereof, are disclosed, wherein $J^1$, $J^2$, B, Y, A and D are as described.
Methods, compositions, and medicaments related thereto are also disclosed.

9 Claims, No Drawings

THERAPEUTIC COMPOUNDS

RELATED APPLICATION

This application claims priority to U.S. Provisional Patent Application Ser. No. 61/036,511 filed on Mar. 14, 2008 and which is incorporated herein in its entirety by this specific reference.

BACKGROUND OF THE INVENTIONS

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

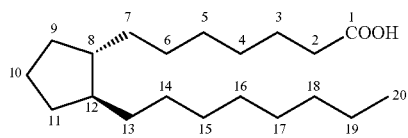

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

The prostaglandin E analog shown below is disclosed in the following documents, expressly incorporated herein by reference: U.S. Pat. No. 5,462,968; U.S. Pat. No. 5,698,598; and U.S. Pat. No. 6,090,847.

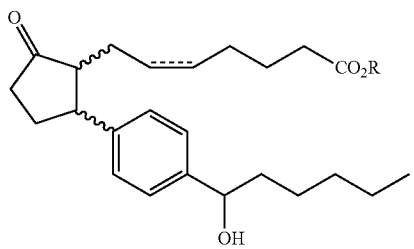

Other $EP_2$ selective agonists are disclosed in U.S. patent application Ser. No. 11/009,298, filed Dec. 10, 2004 (now U.S. Pat. No. 7,091,231 issued Aug. 15, 2006). Prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

SUMMARY OF THE INVENTION

Disclosed herein are compounds useful in treating glaucoma, inflammatory bowel disease, baldness, the stimulation of hair growth, and the stimulation of the conversion of vellus hair to terminal hair. The compounds themselves are disclosed below.

DESCRIPTION OF THE INVENTION

Disclosed herein is a compound having a structure

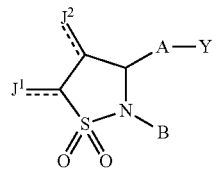

or a pharmaceutically acceptable salt thereof, or a prodrug thereof;
wherein a dashed line represents the presence or absence of a bond;
Y is

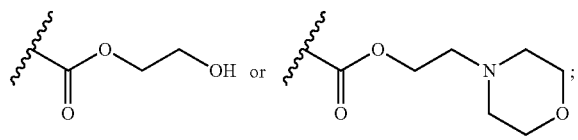

A is —$(CH_2)_6$—, cis —$CH_2CH=CH—(CH_2)_3$—, or —$CH_2C\equiv C—(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;
$J^1$ and $J^2$ are independently H; O; OH; O-alkyl having 1, 2, 3, 4, 5 or 6 carbon atoms; alkyl having 1, 2, 3, 4, 5, or 6 carbon atoms; F; Cl; Br; I; CN; or $CF_3$; and
B is substituted aryl or substituted heteroaryl.

In relation to the identity of A disclosed in the chemical structures presented herein, A is —$(CH_2)_6$—, cis —$CH_2CH=CH—(CH_2)_3$—, or —$CH_2C\equiv C—(CH_2)_3$—, wherein 1 or 2 carbon atoms may be replaced with S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced with S or O.

While not intending to be limiting, A may be —$(CH_2)_6$—, cis —$CH_2CH=CH—(CH_2)_3$—, or —$CH_2C\equiv C—(CH_2)_3$—.

Alternatively, A may be a group which is related to one of these three moieties in that any carbon is replaced with S or O. For example, while not intending to limit the scope of the invention in any way, A may be a moiety where S replaces one or two carbon atoms such as one of the following or the like.

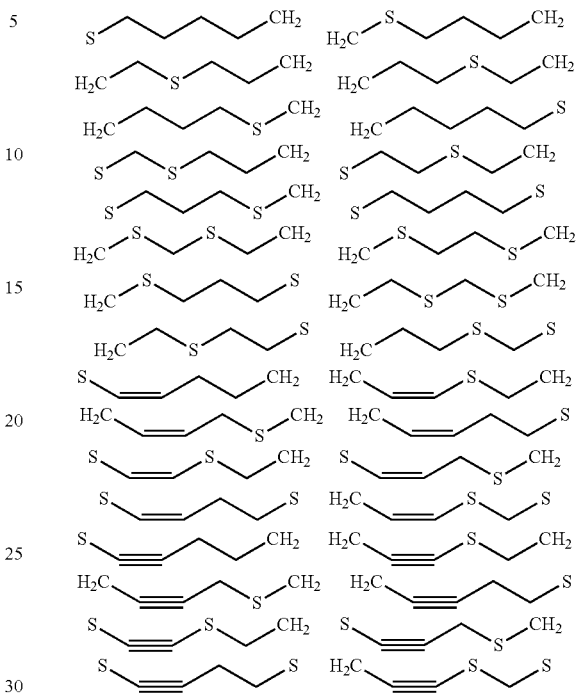

Alternatively, while not intending to limit the scope of the invention in any way, A may be a moiety where O replaces one or two carbon atoms such as one of the following or the like.

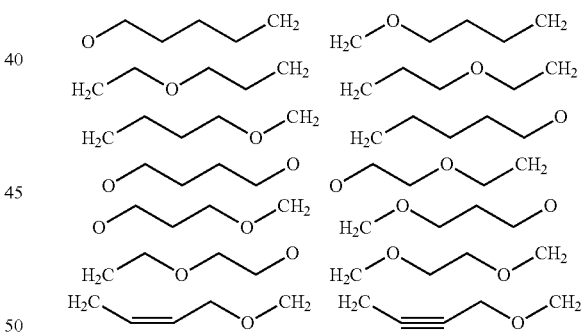

Alternatively, while not intending to limit the scope of the invention in any way, A may have an O replacing one carbon atom and an S replacing another carbon atom, such as one of the following or the like.

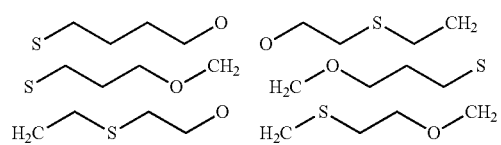

Alternatively, while not intending to limit the scope of the invention in any way, in certain embodiments A is —$(CH_2)_m$—Ar—$(CH_2)_o$—wherein Ar is interarylene or heterointerarylene, the sum of m and o is 1, 2, 3, or 4, and wherein one $CH_2$ may be replaced with S or O. In other words, while not intending to limit the scope of the invention in any way, in one embodiment A comprises 1, 2, 3, or 4 $CH_2$ moieties and Ar, e.g. —$CH_2$—Ar—, —$(CH_2)_2$—Ar—, —$CH_2$—Ar—$CH_2$—, —$CH_2$Ar—$(CH_2)_2$—, —$(CH_2)_2$—Ar—$(CH_2)_2$—, and the like;

in another embodiment A comprises: O; 0, 1, 2, or 3 $CH_2$ moieties; and Ar, e.g., —O—Ar—, Ar—$CH_2$—O—, —O—Ar—$(CH_2)_2$—, —O—$CH_2$—Ar—, —O—$CH_2$—Ar—$(CH_2)_2$, and the like;

in another embodiment A comprises: S; 0, 1, 2, or 3 $CH_2$ moieties; and Ar, e.g., —S—Ar—, Ar—$CH_2$—S—, —S—Ar—$(CH_2)_2$—, —S—$CH_2$—Ar—, —S—$CH_2$—Ar—$(CH_2)_2$, —$(CH_2)_2$—S—Ar, and the like In another embodiment, the sum of m and o is 2, 3, or 4 wherein one $CH_2$ may be replaced with S or O.

In another embodiment, the sum of m and o is 3 wherein one $CH_2$ may be replaced with S or O.

In another embodiment, the sum of m and o is 2 wherein one $CH_2$ may be replaced with S or O.

In another embodiment, the sum of m and o is 4 wherein one $CH_2$ may be replaced with S or O.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —$(CH_2)_2$-Ph-. While not intending to limit scope of the invention in any way, substituents may have 4 or less heavy atoms, wherein the heavy atoms are C, N, O, S, P, F, Cl, Br, and/or I in any stable combination. Any number of hydrogen atoms required for a particular substituent will also be included. A substituent must be stable enough for the compound to be useful as described herein. In addition to the atoms listed above, a substituent may also have a metal cation or any other stable cation having an atom not listed above if the substituent is acidic and the salt form is stable. For example, —OH may form an —$O^-Na^+$ salt or $CO_2H$ may form a $CO_2^-K^+$ salt. Any cation of the salt is not counted in the "4 or less heavy atoms." Thus, the substituent may be hydrocarbyl having up to 4 carbon atoms, including alkyl up to $C_4$, alkenyl, alkynyl, and the like;
hydrocarbyloxy up to $C_3$;
organic acid such as $CO_2H$, $SO_3H$, $P(O)(OH)_2$, and the like, and salts thereof; $CF_3$;
halo, such as F, Cl, or Br;
hydroxyl;
$NH_2$ and alkylamine functional groups up to $C_3$;
other N or S containing substituents such as CN, $NO_2$, and the like; and the like.

In one embodiment A is —$(CH_2)_m$-Ph-$(CH_2)_o$— wherein the sum of m and o is 1, 2, or 3, and wherein one $CH_2$ may be replaced with S or O.

In another embodiment A is —$CH_2$—Ar—$OCH_2$—. In another embodiment A is —$CH_2$-Ph-$OCH_2$—. In another embodiment, Ph is attached at the 1 and 3 positions, otherwise known as m-interphenylene, such as when A has the structure shown below.

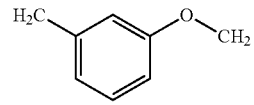

In another embodiment A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced with S or O; or A is —$(CH_2)_2$-Ph- wherein one $CH_2$ may be replaced with S or O.

In another embodiment A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced with S or O; or A is —$(CH_2)_2$-Ph-.

In other embodiments, A has one of the following structures, where Y is attached to the aromatic or heteroaromatic ring.

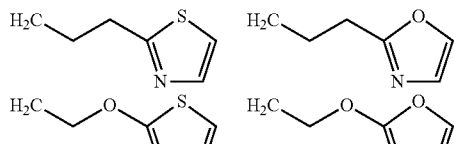
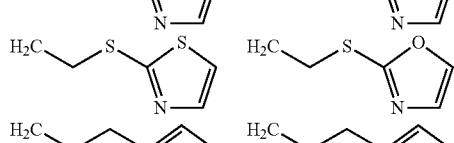
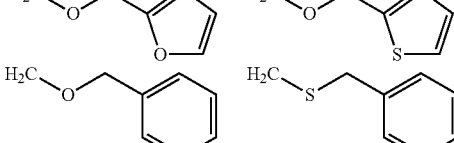
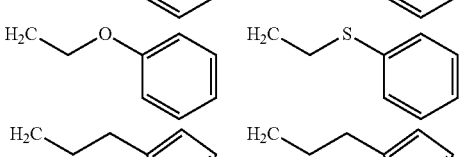

In another embodiment A is —$CH_2OCH_2$Ar.
In another embodiment A is —$CH_2SCH_2$Ar.
In another embodiment A is —$(CH_2)_3$Ar.
In another embodiment A is —$CH_2O(CH_2)_4$.
In another embodiment A is —$CH_2S(CH_2)_4$.
In another embodiment A is —$(CH_2)_6$—.
In another embodiment A is cis —$CH_2CH$=$CH$—$(CH_2)_3$—.
In another embodiment A is —$CH_2C$≡$C$—$(CH_2)_3$—.
In another embodiment A is —$S(CH_2)_3S(CH_2)_2$—.
In another embodiment A is —$(CH_2)_4OCH_2$—.
In another embodiment A is cis —$CH_2CH$=$CH$—$CH_2OCH_2$—.
In another embodiment A is —$CH_2CH$≡$CH$—$CH_2OCH_2$—.
In another embodiment A is —$(CH_2)_2S(CH_2)_3$—.
In another embodiment A is —$CH_2$-Ph-$OCH_2$—, wherein Ph is interphenylene.

In another embodiment A is —CH$_2$-mPh-OCH$_2$—, wherein mPh is m-interphenylene.

In another embodiment A is —CH$_2$—O—(CH2)$_4$—.

In another embodiment A is —CH$_2$—O—CH$_2$—Ar—, wherein Ar is 2,5-interthienylene.

In another embodiment A is —CH$_2$—O—CH$_2$—Ar—, wherein Ar is 2,5-interfurylene.

In another embodiment A is (3-methylphenoxy)methyl.

In another embodiment A is (4-but-2-ynyloxy)methyl.

In another embodiment A is 2-(2-ethylthio)thiazol-4-yl.

In another embodiment A is 2-(3-propyl)thiazol-5-yl.

In another embodiment A is 3-methoxymethyl)phenyl.

In another embodiment A is 3-(3-propyl)phenyl.

In another embodiment A is 3-methylphenethyl.

In another embodiment A is 4-(2-ethyl)phenyl.

In another embodiment A is 4-phenethyl.

In another embodiment A is 4-methoxybutyl.

In another embodiment A is 5-(methoxymethyl)furan-2-yl.

In another embodiment A is 5-(methoxymethyl)thiophen-2-yl.

In another embodiment A is 5-(3-propyl)furan-2-yl.

In another embodiment A is 5-(3-propyl)thiophen-2-yl.

In another embodiment A is 6-hexyl.

In another embodiment A is (Z)-6-hex-4-enyl.

Compounds according to the each of the structures depicted below, and pharmaceutically acceptable salts thereof, and prodrugs thereof, are contemplated as individual embodiments. In other words, each structure represents a different embodiment.

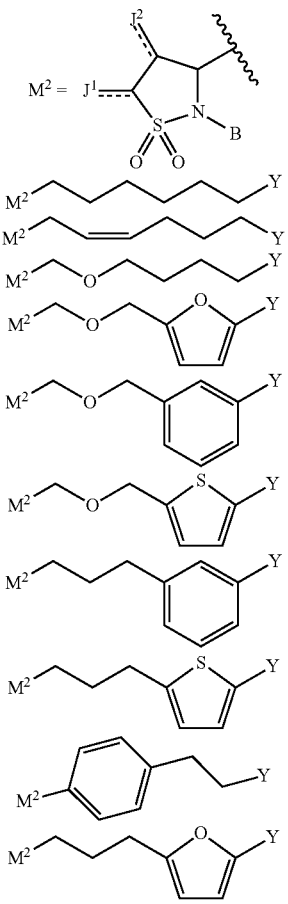

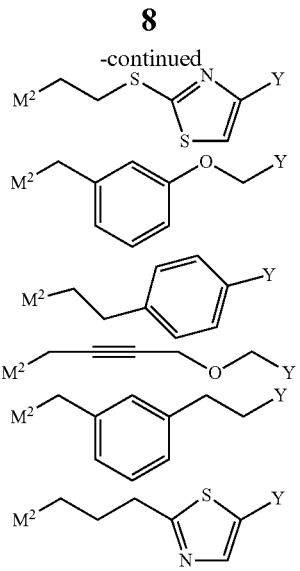

$J^1$ and $J^2$ are independently H; O; OH; O-alkyl having 1, 2, 3, 4, 5 or 6 carbon atoms; alkyl having 1, 2, 3, 4, 5, or 6 carbon atoms; F; Cl; Br; I; CN; or CF$_3$. Thus, each structure depicted below represents a compound embodiment which is individually contemplated. Pharmaceutically acceptable salts and prodrugs of compounds according to the structures below are also contemplated.

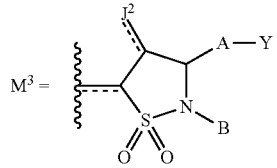

$M^3$=O $M^3$-Cl $M^3$-F $M^3$-Br $M^3$-I $M^3$-CN $M^3$-OH $M^3$-CF$_3$ $M^3$-CH$_3$ $M^3$-C$_2$H$_5$ $M^3$-C$_3$H$_7$ $M^3$-C$_4$H$_9$ $M^3$-OCH$_3$ $M^3$-OC$_2$H$_5$ $M^3$-OC$_3$H$_7$ $M^3$-OC$_4$H$_9$

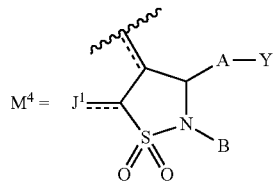

$M^4$=O $M^4$-Cl $M^4$-F $M^4$-Br $M^4$-I $M^4$-CN $M^4$-OH $M^4$-CF$_3$ $M^4$-CH$_3$ $M^4$-C$_2$H$_5$ $M^4$-C$_3$H$_7$ $M^4$-C$_4$H$_9$ $M^4$-OCH$_3$ $M^4$-OC$_2$H$_5$ $M^4$-OC$_3$H$_7$ $M^4$-OC$_4$H$_9$

Aryl is an aromatic ring or ring system such as phenyl, naphthyl, biphenyl, and the like.

Heteroaryl is aryl having one or more N, O, or S atoms in the ring, i.e. one or more ring carbons are substituted by N, O, and/or S. While not intending to be limiting, examples of heteroaryl include thienyl, pyridinyl, furyl, benzothienyl, benzofuryl, imidizololyl, indolyl, and the like.

A substituent of aryl or heteroaryl may have up to 20 non-hydrogen atoms each in any stable combination and as many hydrogen atoms as necessary, wherein the non-hydrogen atoms are C, N, O, S, P, F, Cl, Br, and/or I in any stable combination. However, the total number of non-hydrogen atoms on all of the substituents combined must also be 20 or less. A substituent must be sufficiently stable for the compound to be useful as described herein. In addition to the atoms listed above, a substituent may also have a metal cation or other stable cation having an atom not listed above if the substituent is acidic and the salt form is stable. For example, —OH may form an —O$^-$Na$^+$ salt or CO$_2$H may form a CO$_2{}^-$K$^+$ salt. Thus, while not intending to limit the scope of the invention in any way, a substituent may be:

hydrocarbyl, i.e. a moiety consisting of only carbon and hydrogen such as alkyl, alkenyl, alkynyl, and the like, including linear, branched or cyclic hydrocarbyl, and combinations thereof;

hydrocarbyloxy, meaning O-hydrocarbyl such as OCH$_3$, OCH$_2$CH$_3$, O-cyclohexyl, etc, up to 19 carbon atoms;

other ether substituents such as CH$_2$OCH$_3$, (CH$_2$)$_2$OCH (CH$_3$)$_2$, and the like;

thioether substituents including S-hydrocarbyl and other thioether substituents;

hydroxyhydrocarbyl, meaning hydrocarbyl-OH such as CH$_2$OH, C(CH$_3$)$_2$OH, etc, up to 19 carbon atoms;

nitrogen substituents such as NO$_2$, CN, and the like, including amino, such as NH$_2$, NH(CH$_2$CH$_3$OH), NHCH$_3$, and the like;

carbonyl substituents, such as CO$_2$H, ester, amide, and the like;

halogen, such as chloro, fluoro, bromo, and the like fluorocarbyl, such as CF$_3$, CF$_2$CF$_3$, etc.;

phosphorous substituents, such as PO$_3{}^{2-}$, and the like;

sulfur substituents, including S-hydrocarbyl, SH, SO$_3$H, SO$_2$-hydrocarbyl, SO$_3$-hydrocarbyl, and the like.

Substituted aryl or heteroaryl may have as many substituents as the ring or ring system will bear, and the substituents may be the same or different. Thus, for example, an aryl ring or a heteroaryl ring may be substituted with chloro and methyl; methyl, OH, and F; CN, NO$_2$, and ethyl; and the like including any conceivable substituent or combination of substituent possible in light of this disclosure.

Substituted aryl or substituted heteroaryl also includes a bicyclic or polycyclic ring system wherein one or more rings are aromatic and one or more rings are not. For example, indanonyl, indanyl, indanolyl, tetralonyl, and the like are substituted aryl. For this type of polycyclic ring system, an aromatic or heteroaromatic ring, not a non-aromatic ring, must be attached to the remainder of the molecule, i.e. the part of the molecule that is not B. In other words, in any structure depicting—B herein, where — is a bond, the bond is a direct bond to an aromatic ring.

In one embodiment, B is substituted aryl or heteroaryl.
In another embodiment B is substituted phenyl.
In another embodiment B has no halogen atoms.
In another embodiment B is 4-(1-hydroxy-2,2-dimethylpropyl)phenyl.
In another embodiment B is 4-(1-hydroxy-2-methylpropan-2-yl)phenyl.
In another embodiment B is 4-(1-hydroxy-2-methylpropyl)phenyl.
In another embodiment B is 4-(1-hydroxybutyl)phenyl.
In another embodiment B is 4-(1-hydroxyheptyl)phenyl.
In another embodiment B is 4-(1-hydroxyhexyl)phenyl.
In another embodiment B is 4-(1-hydroxypentyl)phenyl.
In another embodiment B is 4-(1-hydroxypropyl)phenyl.
In another embodiment B is 4-(3-hydroxy-2-methylheptan-2-yl)phenyl.
In another embodiment B is 4-(3-hydroxy-2-methyloctan-2-yl)phenyl.
In another embodiment B is 1-hydroxy-2,3-dihydro-1H-inden-5-yl.
In another embodiment B is 2,3-dihydro-1H-inden-5-yl.
In another embodiment B is 3-(hydroxy(1-propylcyclobutyl)methyl)phenyl.
In another embodiment B is 4-(1-hydroxy-5,5-dimethylhexyl)phenyl.
In another embodiment B is 4-(hydroxy(1-propylcyclobutyl)methyl)phenyl.
In another embodiment B is 4-tert-butylphenyl.
In another embodiment B is 4-hexylphenyl.
In another embodiment B is 4-(1-hydroxy-2-phenylethyl)phenyl.
In another embodiment B is 4-(1-hydroxy-3-phenylpropyl)phenyl.
In another embodiment B is 4-(1-hydroxycyclobutyl)phenyl.
In another embodiment B is 4-(2-cyclohexyl-1-hydroxyethyl)phenyl.
In another embodiment B is 4-(3-cyclohexyl-1-hydroxypropyl)phenyl.
In another embodiment B is 4-(cyclohexyl(hydroxy)methyl)phenyl.
In another embodiment B is 4-(cyclohexylmethyl)phenyl.
In another embodiment B is 4-(hydroxy(phenyl)methyl)phenyl.

Another embodiment is a compound according to the structure

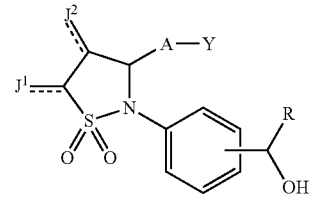

or a pharmaceutical salt thereof, or a prodrug thereof, wherein R is hydrogen or C1-10 hydrocarbyl.

Another embodiment is a compound according to the structure

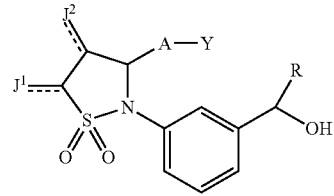

or a pharmaceutical salt thereof, or a prodrug thereof, wherein R is hydrogen or C1-10 hydrocarbyl.

Another embodiment is a compound according to the structure

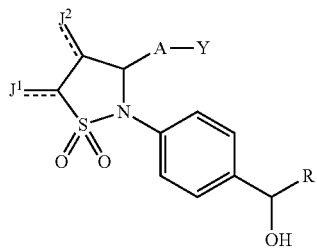

or a pharmaceutical salt thereof, or a prodrug thereof, wherein R is hydrogen or C1-10 hydrocarbyl.

Another embodiment is a compound according to the structure

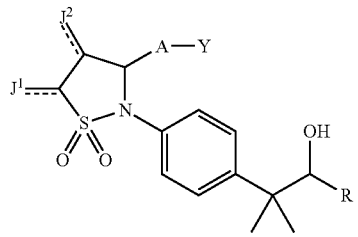

or a pharmaceutical salt thereof, or a prodrug thereof, wherein R is hydrogen or C1-10 hydrocarbyl.

"C1-10" hydrocarbyl is hydrocarbyl having 1, 2, 3, 4, 5, 6, 7, 8, 9, or 10 carbon atoms.

Hydrocarbyl is a moiety consisting of only carbon and hydrogen, and includes, but is not limited to alkyl, alkenyl, alkynyl, and the like, and in some cases aryl, and combinations thereof.

Alkyl is hydrocarbyl having no double or triple bonds including:

linear alkyl such as methyl, ethyl, propyl, n-butyl, n-pentyl, n-hexyl, and the like;

branched alkyl such as isopropyl, branched butyl isomers (i.e. sec-butyl, tert-butyl, etc), branched pentyl isomers (i.e. iso-pentyl, etc), branched hexyl isomers, and higher branched alkyl fragments;

cycloalkyl such as cyclopropyl, cyclobutyl, cyclopentyl, cyclohexyl, cycloheptyl, etc.; and alkyl fragments consisting of both cyclic and noncyclic components, whether linear or branched, which may be attached to the remainder of the molecule at any available position including terminal, internal, or ring carbon atoms.

Alkenyl is hydrocarbyl having one or more double bonds including linear alkenyl, branched alkenyl, cyclic alkenyl, and combinations thereof in analogy to alkyl.

Alkynyl is hydrocarbyl having one or more triple bonds including linear alkynyl, branched alkynyl, cyclic alkynyl and combinations thereof in analogy to alkyl.

Aryl is an unsubstituted or substituted aromatic ring or ring system such as phenyl, naphthyl, biphenyl, and the like. Aryl may or may not be hydrocarbyl, depending upon whether it has substituents with heteroatoms.

Arylalkyl is alkyl which is substituted with aryl. In other words alkyl connects aryl to the remaining part of the molecule. Examples are —CH$_2$-Phenyl, —CH$_2$—CH$_2$-Phenyl, and the like. Arylalkyl may or may not be hydrocarbyl, depending upon whether the aryl portion has substituents with heteroatoms.

Unconjugated dienes or polyenes have one or more double bonds which are not conjugated. They may be linear, branched, or cyclic, or a combination thereof. Combinations of the above are also possible.

Thus, each of the structures below is contemplated. These structures, or pharmaceutically acceptable salts thereof, or prodrugs thereof, individually represent a compound which is an embodiment contemplated herein. In other words, each structure represents a different embodiment.

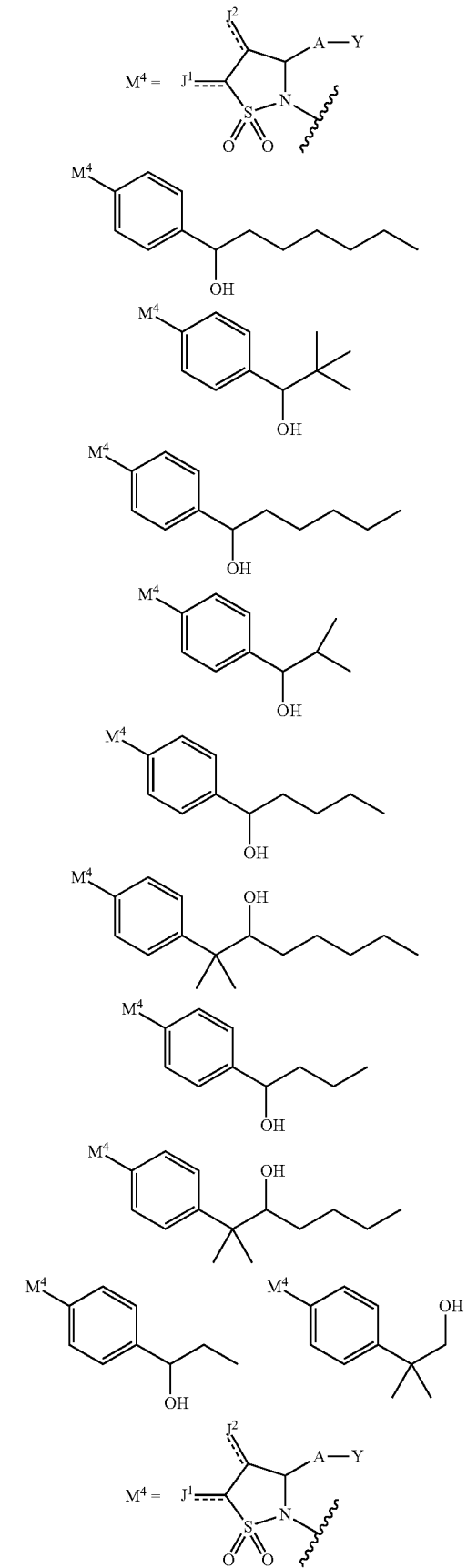

-continued
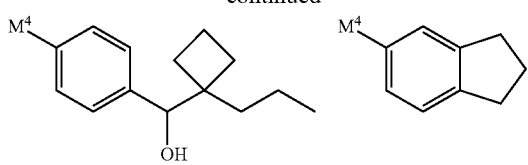
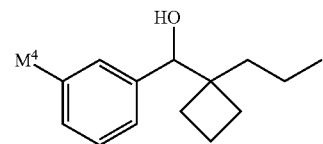
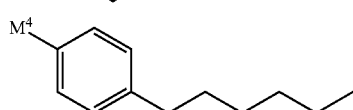
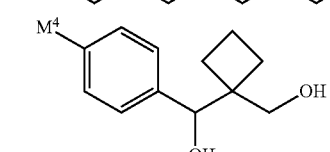
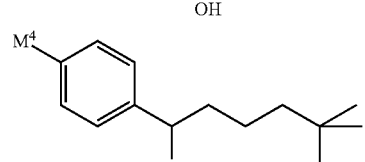
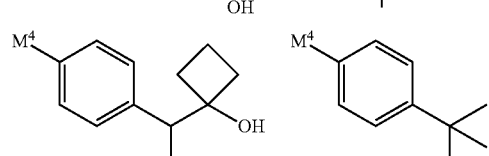
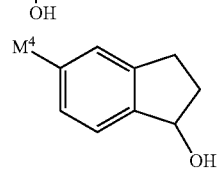
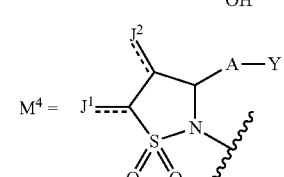
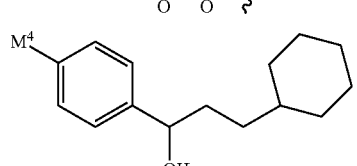
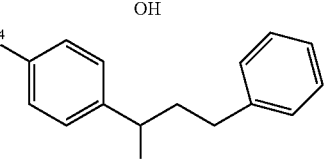
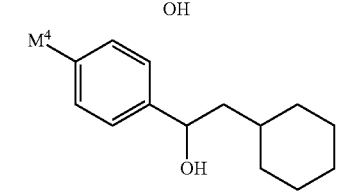
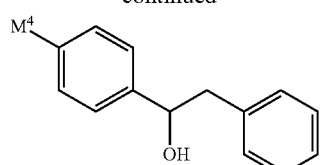
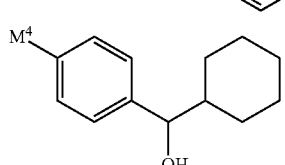
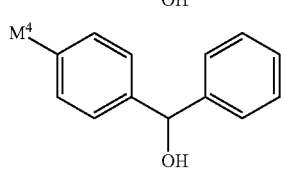
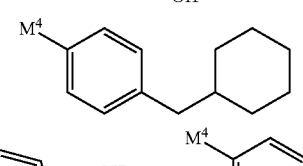
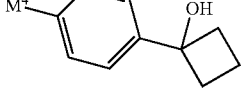
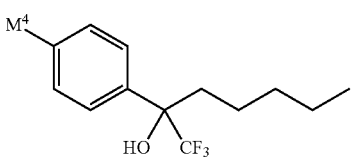
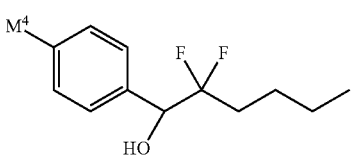
In the above embodiments, x is 5, 6, or 7, and y+z is 2x+1.
In one embodiment, x is 5 and y+z is 11.
In another embodiment, x is 6 and y+z is 13.
In another embodiment, x is 7 and y+z is 15.
Hypothetical examples of useful compounds are shown below.
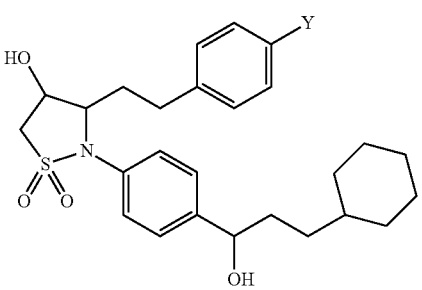

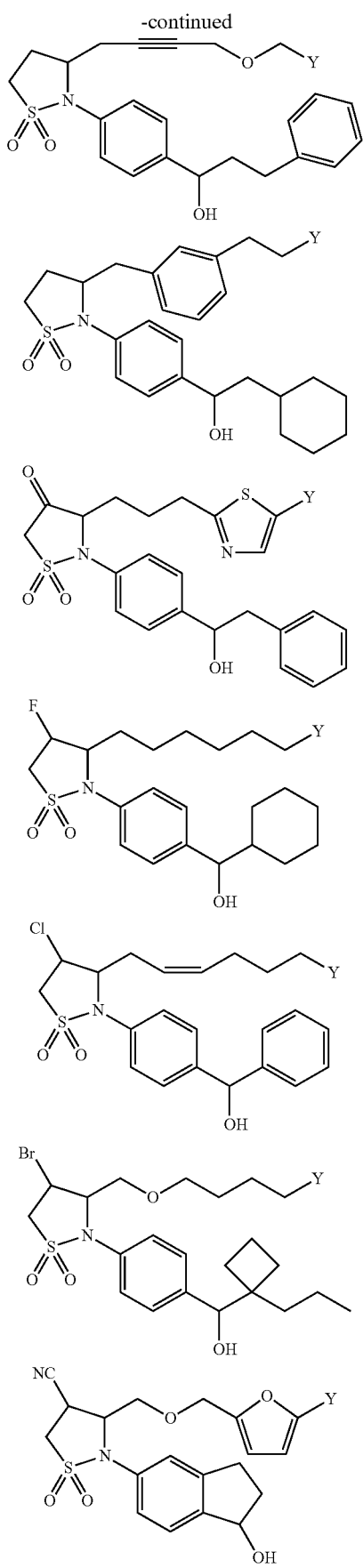

17
-continued
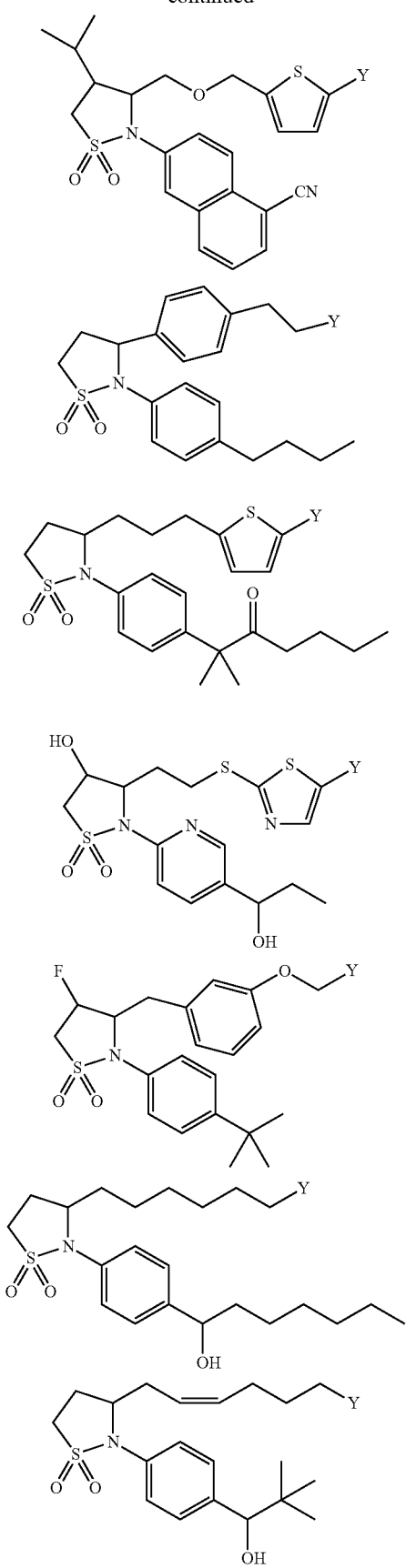
18
-continued
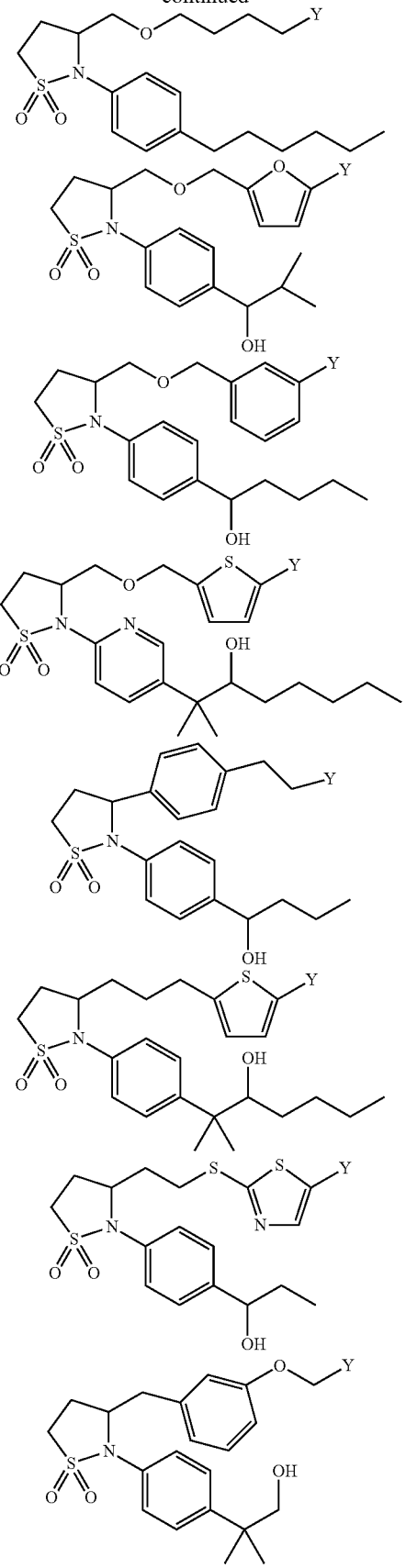

COMPOUND EXAMPLES

The following are hypothetical examples of useful compounds:

Compound Example 1

A compound having a structure

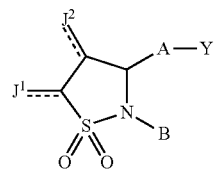

or a pharmaceutically acceptable salt thereof, or a prodrug thereof;
wherein a dashed line represents the presence or absence of a bond;
Y is

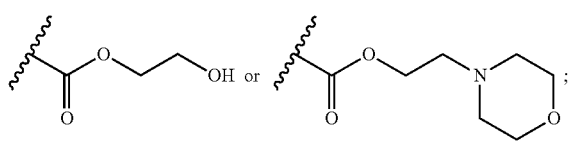

A is $-(CH_2)_6-$, cis $-CH_2CH=CH-(CH_2)_3-$, or $-CH_2C\equiv C-(CH_2)_3-$, wherein 1 or 2 carbon atoms may be replaced by S or O; or A is $-(CH_2)_m-Ar-(CH_2)_o-$ wherein Ar is interarylene or heterointerarylene, the sum of m and o is 1, 2, 3, or 4, and wherein one $CH_2$ may be replaced by S or O;
$J^1$ and $J^2$ are independently H; O; OH; O-alkyl having 1, 2, 3, 4, 5 or 6 carbon atoms;
alkyl having 1, 2, 3, 4, 5, or 6 carbon atoms; F; Cl; Br; I; CN; or $CF_3$; and
B is substituted aryl or substituted heteroaryl.

Compound Example 2

The compound according to compound example 1 wherein B is substituted phenyl.

Compound Example 3

The compound according to compound example 1 having a structure

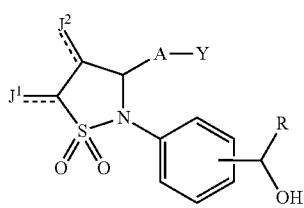

or a pharmaceutically acceptable salt thereof, or a prodrug thereof;
wherein R is hydrogen or $C_{1-10}$ hydrocarbyl.

Compound Example 4

The compound according to compound example 3 wherein R is alkyl.

Compound Example 5

The compound according to compound example 3 wherein R is arylalkyl.

Compound Example 6

The compound according to compound example any one of compound examples 1 to 5 having a structure

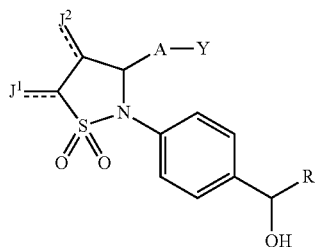

or a pharmaceutically acceptable salt thereof, or a prodrug thereof;
wherein R is hydrogen or $C_{1-10}$ hydrocarbyl.

Compound Example 7

The compound according to compound example 1 wherein A is (3-methylphenoxy)methyl.

Compound Example 8

The compound according to compound example 1 wherein A is (4-but-2-ynyloxy)methyl.

Compound Example 9

The compound according to compound example 1 wherein A is 2-(2-ethylthio)thiazol-4-yl.

Compound Example 10

The compound according to compound example 1 wherein A is 2-(3-propyl)thiazol-5-yl.

Compound Example 11

The compound according to compound example 1 wherein A is 3-methoxymethyl)phenyl.

Compound Example 12

The compound according to compound example 1 wherein A is 3-(3-propylphenyl.

Compound Example 13

The compound according to compound example 1 wherein A is 3-methylphenethyl.

Compound Example 14

The compound according to compound example 1 wherein A is 4-(2-ethyl)phenyl.

Compound Example 15

The compound according to compound example 1 wherein A is 4-phenethyl.

Compound Example 16

The compound according to compound example 1 wherein A is 4-methoxybutyl.

Compound Example 17

The compound according to compound example 1 wherein A is 5-(methoxymethyl)furan-2-yl.

Compound Example 18

The compound according to compound example 1 wherein A is 5-(methoxymethyl)thiophen-2-yl.

Compound Example 19

The compound according to compound example 1 wherein A is 5-(3-propyl)furan-2-yl.

Compound Example 20

The compound according to compound example 1 wherein A is 5-(3-propyl)thiophen-2-yl.

Compound Example 21

The compound according to compound example 1 wherein A is 6-hexyl.

Compound Example 22

The compound according to compound example 1 wherein A is (Z)-6-hex-4-enyl.

Compound Example 23

The compound according to any one of compound examples 1 and 7-22 wherein B is 4-(1v-hydroxy-2,2-dimethylpropyl)phenyl.

Compound Example 24

The compound according to any one of compound examples 1 and 7-22 wherein B is 4-(1-hydroxy-2-methylpropan-2-yl)phenyl.

Compound Example 25

The compound according to any one of compound examples 1 and 7-22 wherein B is 4-(1-hydroxy-2-methylpropyl)phenyl.

Compound Example 26

The compound according to any one of compound examples 1 and 7-22 wherein B is 4-(1-hydroxybutyl)phenyl.

Compound Example 27

The compound according to any one of compound examples 1 and 7-22 wherein B is 4-(1-hydroxyheptyl)phenyl.

Compound Example 28

The compound according to any one of compound examples 1 and 7-22 wherein B is 4-(1-hydroxyhexyl)phenyl.

Compound Example 29

The compound according to any one of compound examples 1 and 7-22 wherein B is 4-(1-hydroxypentyl)phenyl.

Compound Example 30

The compound according to any one of compound examples 1 and 7-22 wherein B is 4-(1-hydroxypropyl)phenyl.

Compound Example 31

The compound according to any one of compound examples 1 and 7-22 wherein B is 4-(3-hydroxy-2-methylheptan-2-yl)phenyl.

Compound Example 32

The compound according to any one of compound examples 1 and 7-22 wherein B is 4-(3-hydroxy-2-methyloctan-2-yl)phenyl.

Compound Example 33

The compound according to any one of compound examples 1 and 7-22 wherein B is 1-hydroxy-2,3-dihydro-1H-inden-5-yl.

Compound Example 34

The compound according to any one of compound examples 1 and 7-22 wherein B is 2,3-dihydro-1H-inden-5-yl.

Compound Example 35

The compound according to any one of compound examples 1 and 7-22 wherein B is 3-(hydroxy(1-propylcyclobutyl)methyl)phenyl.

Compound Example 36

The compound according to any one of compound examples 1 and 7-22 wherein B is 4-(1-hydroxy-5,5-dimethylhexyl)phenyl.

Compound Example 37

The compound according to any one of compound examples 1 and 7-22 wherein B is 4-(hydroxy(1-propylcyclobutyl)methyl)phenyl.

Compound Example 38

The compound according to any one of compound examples 1 and 7-22 wherein B is 4-tert-butylphenyl.

Compound Example 39

The compound according to any one of compound examples 1 and 7-22 wherein B is 4-hexylphenyl.

Compound Example 40

The compound according to any one of compound examples 1 and 7-22 wherein B is 4-(1-hydroxy-2-phenylethyl)phenyl.

Compound Example 41

The compound according to any one of compound examples 1 and 7-22 wherein B is 4-(1-hydroxy-3-phenylpropyl)phenyl.

Compound Example 42

The compound according to any one of compound examples 1 and 7-22 wherein B is 4-(1-hydroxycyclobutyl)phenyl.

Compound Example 43

The compound according to any one of compound examples 1 and 7-22 wherein B is 4-(2-cyclohexyl-1-hydroxyethyl)phenyl.

Compound Example 44

The compound according to any one of compound examples 1 and 7-22 wherein B is 4-(3-cyclohexyl-1-hydroxypropyl)phenyl.

Compound Example 45

The compound according to any one of compound examples 1 and 7-22 wherein B is 4-(cyclohexyl(hydroxy)methyl)phenyl.

Compound Example 46

The compound according to any one of compound examples 1 and 7-22 wherein B is 4-(cyclohexylmethyl)phenyl.

Compound Example 47

The compound according to any one of compound examples 1 and 7-22 wherein B is 4-(hydroxy(phenyl)methyl)phenyl.

Compound Example 48

The compound according to any one of compound examples 1 to 47 wherein $J^1$ is H.

Compound Example 49

The compound according to any one of compound examples 1 to 47 wherein $J^1$ is O.

Compound Example 50

The compound according to any one of compound examples 1 to 47 wherein $J^1$ is OH.

Compound Example 51

The compound according to any one of compound examples 1 to 47 wherein $J^1$ is O-alkyl having 1, 2, 3, 4, 5 or 6 carbon atoms.

Compound Example 52

The compound according to any one of compound examples 1 to 47 wherein $J^1$ is alkyl having 1, 2, 3, 4, 5, or 6 carbon atoms.

Compound Example 53

The compound according to any one of compound examples 1 to 47 wherein $J^1$ is F.

Compound Example 54

The compound according to any one of compound examples 1 to 47 wherein $J^1$ is Cl.

Compound Example 55

The compound according to any one of compound examples 1 to 47 wherein $J^1$ is Br.

Compound Example 56

The compound according to any one of compound examples 1 to 47 wherein $J^1$ is I.

Compound Example 57

The compound according to any one of compound examples 1 to 47 wherein $J^1$ is CN.

Compound Example 58

The compound according to any one of compound examples 1 to 47 wherein $J^1$ is $CF_3$.

Compound Example 59

The compound according to any one of compound examples 1 to 58 wherein $J^2$ is H.

Compound Example 60

The compound according to any one of compound examples 1 to 58 wherein $J^2$ is O.

Compound Example 61

The compound according to any one of compound examples 1 to 58 wherein $J^2$ is OH.

Compound Example 62

The compound according to any one of compound examples 1 to 58 wherein $J^2$ is O-alkyl having 1, 2, 3, 4, 5 or 6 carbon atoms.

Compound Example 63

The compound according to any one of compound examples 1 to 58 wherein $J^2$ is alkyl having 1, 2, 3, 4, 5, or 6 carbon atoms.

Compound Example 64

The compound according to any one of compound examples 1 to 58 wherein $J^2$ is F.

Compound Example 65

The compound according to any one of compound examples 1 to 58 wherein $J^2$ is Cl.

Compound Example 66

The compound according to any one of compound examples 1 to 58 wherein $J^2$ is Br.

Compound Example 67

The compound according to any one of compound examples 1 to 58 wherein $J^2$ is I.

Compound Example 68

The compound according to any one of compound examples 1 to 58 wherein $J^2$ is CN.

Compound Example 69

The compound according to any one of compound examples 1 to 58 wherein $J^2$ is $CF_3$.

The following are hypothetical examples of compositions, kits, methods, uses, and medicaments employing the hypothetical compound examples.

Composition Example

A composition comprising a compound according to any one of compound examples 1 to 69, wherein said composition is a liquid which is ophthalmically acceptable.

Medican Examples

Use of a compound according to any one of compound examples 1 to 69 in the manufacture of a medicament for the treatment of glaucoma or ocular hypertension in a mammal.

Use of a compound according to any one of compound examples 1 to 69 in the manufacture of a medicament for the treatment of baldness in a person.

A medicament comprising a compound according to any one of compound examples 1 to 69, wherein said composition is a liquid which is ophthalmically acceptable.

Method Example

A method comprising administering a compound according to any one of compound examples 1 to 69 to a mammal for the treatment of glaucoma or ocular hypertension.

Kit Example

A kit comprising a composition comprising compound according to any one of compound examples 1 to 70, a container, and instructions for administration of said composition to a mammal for the treatment of glaucoma or ocular hypertension.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of $C_1$ (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physiogicla acceptable osmolarity by addition of pharmaceutically acceptable buffers and salts. Such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

For treatment of diseases affecting the eye including glaucoma, these compounds can be administered topically, periocularly, intraocularly, or by any other effective means known in the art.

These compounds may be prepared by a number of methods known in the art. For example, PCT Application No PCT/US2006/007797, filed on Mar. 6, 2006, which claims priority to U.S. Provision Patent Application 60/660,748, filed on Mar. 10, 2005, both of which expressly incorporated herein by reference; and U.S. Pat. No. 4,087,435, which is expressly incorporated herein by reference, may be adapted to prepare the compounds disclosed herein. Schemes 1 and 2 show a typical example of a method of preparing these compounds using methods adapted from these references. Other methods are apparent to those of ordinary skill in the art.

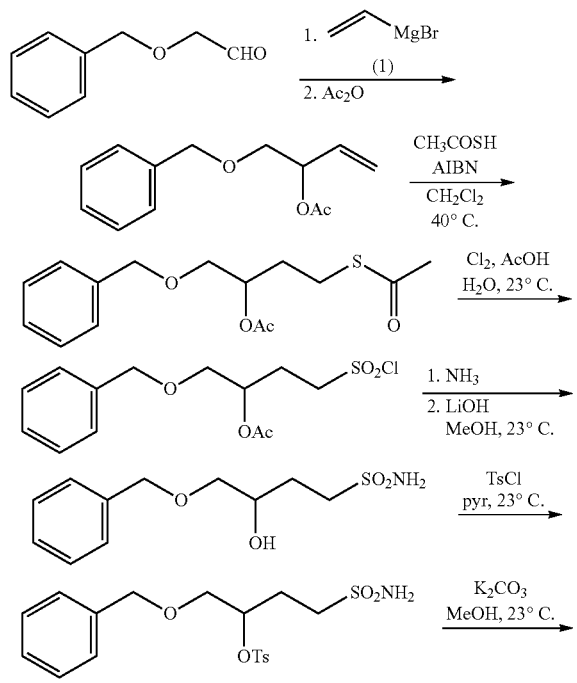

Scheme 1

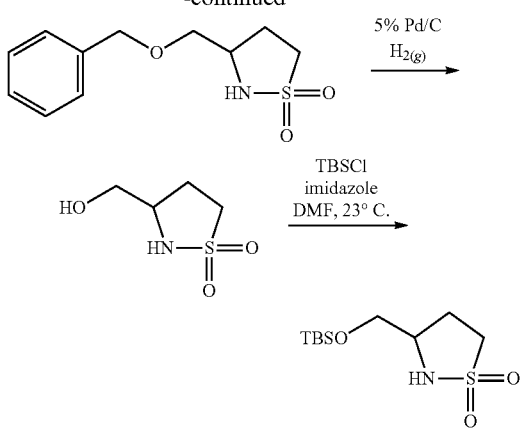

(1) U.S. Pat. No. 4,087,435

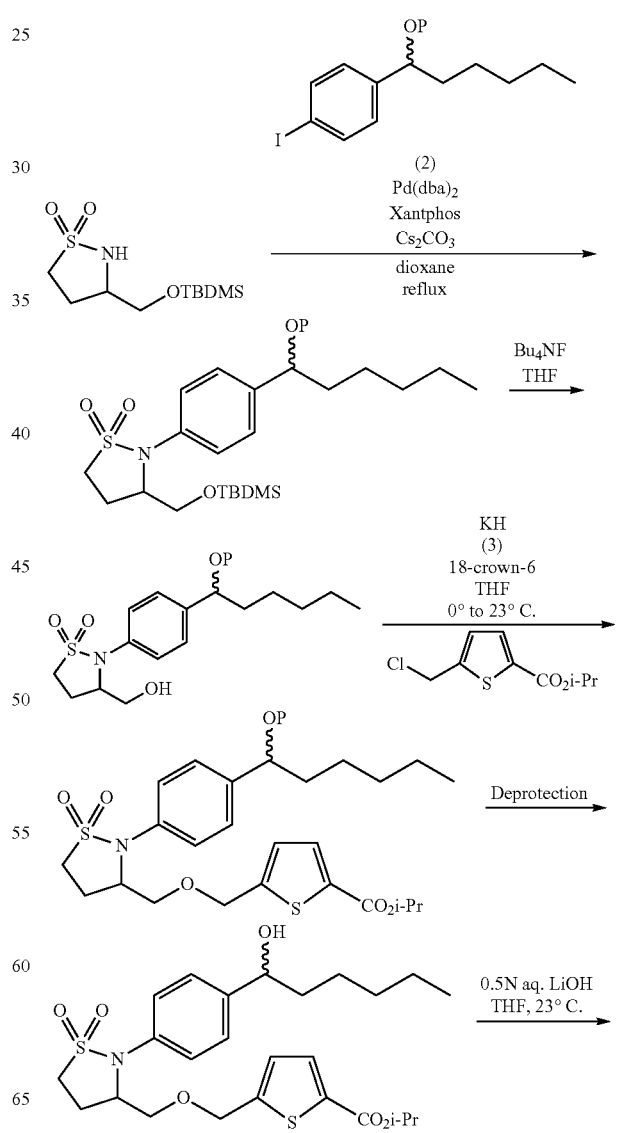

Scheme 2

33

-continued

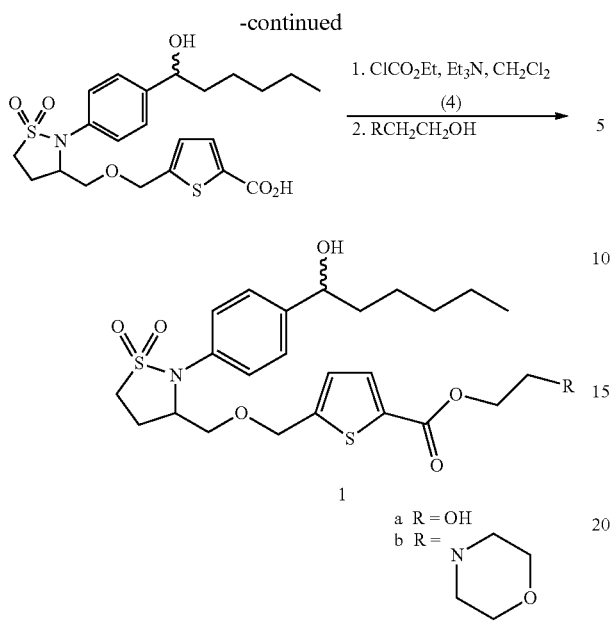

(2) Tet. Lett. 2004, 3305-7
(3) U.S. Provisional Application No. 60/660,748
(4) U.S. Provisional Application No. 60/022,172

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer."

In Vivo Examples

Compounds 1a and 1b from above are tested in vivo to measure its ability to reduce intraocular pressure. Compound 1a is tested in normotensive dogs. The intraocular pressure (IOP) decreases from baseline. This compound is also tested in laser-induced hypertensive monkeys, the IOP decreases from baseline.

Compound 1b is tested in normotensive dogs. The IOP decreases from baseline. This compound is also tested in laser-induced hypertensive monkeys, the IOP decreases from baseline.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

34

What is claimed is:

1. A compound which is a structure

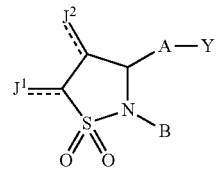

or a pharmaceutically acceptable salt thereof;
wherein a dashed line represents the presence or absence of a bond;
Y is

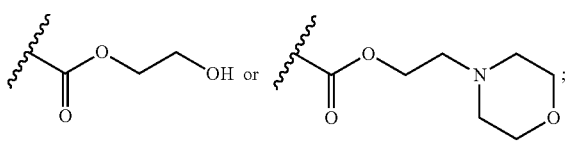

A is —$(CH_2)_6$—, cis —$CH_2CH=CH—(CH_2)_3$—, or —$CH_2C\equiv C—(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;

$J^1$ and $J^2$ are independently H; O; OH; O-alkyl having 1, 2, 3, 4, 5 or 6 carbon atoms; alkyl having 1, 2, 3, 4, 5, or 6 carbon atoms; F; Cl; Br; I; CN; or $CF_3$; and B is substituted aryl or substituted heteroaryl.

2. The compound according to claim 1 which is a structure

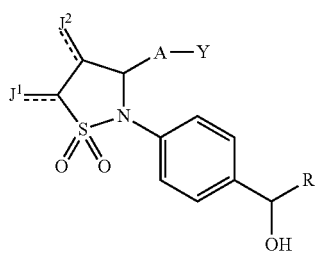

or a pharmaceutically acceptable salt thereof;
wherein R is hydrogen or $C_{1-10}$ hydrocarbyl.

3. The compound according to claim 1 having a structure

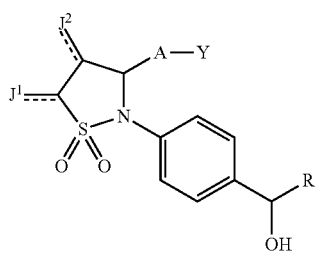

or a pharmaceutically acceptable salt thereof;
wherein R is hydrogen or $C_{1-10}$ hydrocarbyl.

4. The compound according to claim 1 which is a structure

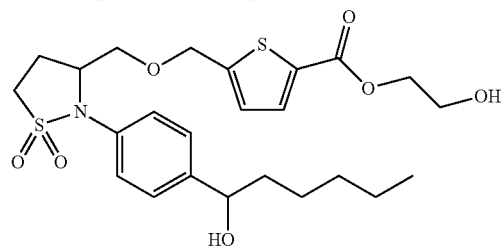

or a pharmaceutically acceptable salt thereof.

5. The compound according to claim 1 which is a structure

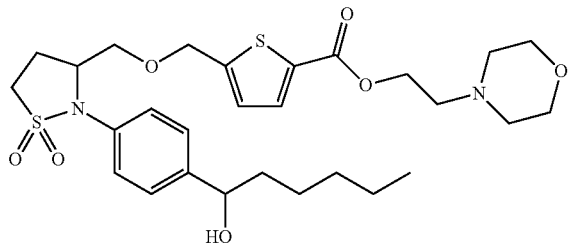

or a pharmaceutically acceptable salt thereof.

6. The compound according to claim 1 which is a structure

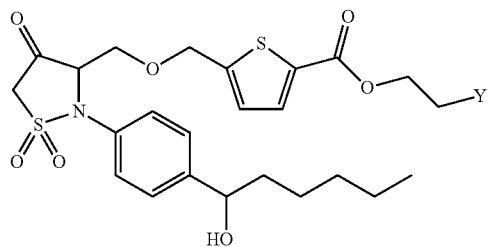

or a pharmaceutically acceptable salt thereof.

7. The compound according to claim 1 which is a structure

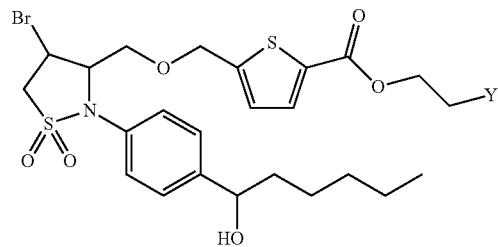

or a pharmaceutically acceptable salt thereof.

8. The compound according to claim claim 1 which is a structure

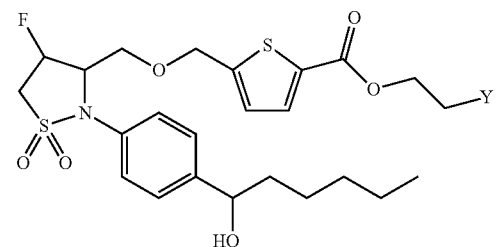

or a pharmaceutically acceptable salt thereof.

9. A method of treating baldness using a compound according to claim 1.

* * * * *